United States Patent [19]

Gero

[11] Patent Number: 4,693,705
[45] Date of Patent: Sep. 15, 1987

[54] VAGINAL CONTRACEPTIVE SYSTEM
[76] Inventor: Ilona B. Gero, 300 Park Ave. South, Suite 1410, New York, N.Y. 10010
[21] Appl. No.: 884,753
[22] Filed: Jul. 11, 1986

Related U.S. Application Data

[63] Continuation of Ser. No. 598,208, Apr. 9, 1984, abandoned.
[51] Int. Cl.[4] ............................................. A61M 31/00
[52] U.S. Cl. ........................................ 604/55; 604/286
[58] Field of Search ................. 604/55, 286, 287, 288, 604/359, 360, 368, 904

[56] References Cited

U.S. PATENT DOCUMENTS

| | | | |
|---|---|---|---|
| 3,490,545 | 1/1970 | Goldfarb et al. | 604/359 |
| 3,639,566 | 2/1972 | Naito et al. | 604/55 |
| 3,949,752 | 4/1976 | Van Stee | 604/286 |
| 4,228,797 | 10/1980 | Dickey | 604/55 |
| 4,351,338 | 9/1982 | Langlois et al. | 604/904 |
| 4,393,871 | 7/1983 | Vorhauer et al. | 604/55 |

Primary Examiner—C. Fred Rosenbaum
Assistant Examiner—Sherri Vinyard
Attorney, Agent, or Firm—Jacobs & Jacobs

[57] ABSTRACT

The invention features an innovative vaginal sponge contraceptive device that has active spermicide. The active spermicide allows the device to be used instantly upon removal from its sealed packet. The sponge is of a sufficient size such that swelling agents, contained therein, maintain the sponge in pressured contact with the vaginal wall to prevent slippage from cervical contact. A low level of spermicide allows for effectiveness without irritation. A deodorant, contained in the sponge, provides for continuous use over a 24-hour period.

6 Claims, 6 Drawing Figures

VAGINAL CONTRACEPTIVE SYSTEM

This is a continuation of Ser. No. 598,208 filed 4-9-84, now abandoned.

TECHNICAL FIELD

This invention relates to a vaginal contraceptive system, and more particulary to a safe, ready-to-use, sponge-type vaginal insert containing an active spermicide.

BACKGROUND ART

Recent clinical studies have indicated that young women using oral contraceptives may increase their risk of developing breast and cervical cancers in mid-life. These studies have caused anxiety in many women.

Whether this type of contraception is dangerous or not will be the subject of debates for many years to come. One fact was certain, however, the "pill" did interfere with the hormonal balance of the user. Side effects from the use of oral contraceptives have been observed in many women.

Attempts to find safer contraceptive methods have been under study. Recently, a 24-hour vaginal contraceptive sponge has been commercially marketed. The device comprised a polyurethane disc having a central recess and containing 1,000 milligrams of a spermicide known as nonoxynol-9, which was more generically known as nonylphenoxypoly (ethyleneoxy) ethanol.

This type of contraceptive is statistically comparable to the effectiveness reported for that of a diaphragm and prevents pregenancy in three basic ways:

(1) The nonylphenoxypoly (ethyleneoxy) ethanol kills the sperm;
(2) The sponge blocks the cervix and prevents sperm penetration of the uterus; and
(3) The sponge traps and absorbs the sperm.

While the sponge has met with some success in the market place, its usage has been accompanied by drawbacks. Use of this device required that the spermicide be activated by adding tap water. The mandate for such procedure presented numerous disadvantages:

(a) The spermicide was often diluted, and application of a uniform amount of active spermicide is often unpredictable depending upon the amount of water run through the sponge;
(b) The tap water contained bacteria that destroyed or impaired the sterility of the sponge;
(c) The water contained chemicals, such as chlorine and flourides, that possibly interfered and reacted with the substances contained in the sponge; and
(d) The sponge could not be immediately inserted or used after removal from its package, i.e., the sponge did not contain active spermicide.

In addition, the use of 1,000 milligrams of nonoxynol-9 is believed to be excessive, and may cause irritation and allergic reactions.

The sponge-type contraceptive of the present invention is designated to eliminate or substantially reduce all of the aforementioned disadvantages. The contraceptive is packaged in a sealed, bacteria-free, foil packet. Its spermicide is already activated and carried in a solution of distilled water so that the sponge can be immediately used upon removal from its packet. With this procedure, the spermicide of the present invention remains sterile, its dosage is reliable, uniform and effective.

The contraceptive system of the invention contains no greater than approximately 100 milligrams of spermicide, so that optimal spermicidal action is achieved while minimizing the possibility of irritation to the vaginal vault.

Other important innovations of the present invention will be described hereinafter.

DISCLOSURE OF THE INVENTION

The invention pertains to a vaginal contraceptive system featuring a porous, sponge mass for insertion into the vaginal vault, and for contacting and blocking the cervix. The sponge is of a sufficient size and contains at least one swelling agent, so that the sponge will exert radial pressure against the vaginal wall. Such pressure will maintain the contact established between the sponge and the cervix, prevent dislodgement and provide an effective barrier against sperm penetration.

The sponge is comprised of a generally spheroid mass of polyurethane, approximately 1.5 to 2.0 inches in diameter.

A drawstring is attached to the sponge in a reticulated fashion, and provides a means for withdrawal after use. The drawstring is looped diametrically through the sponge and, when tightened, compresses an area of the sponge.

The contraceptive can be immediately used after removal from its container. This is accomplished by utilizing a sealed packet, and by employing an active spermicide, i.e., the spermicide is already in solution within the sponge.

Sterility is maintained by the sealed packet and the bacteria-free, distilled water base used to carry the spermicide. The spermicidal action is achieved with a minimum possibility of irritation to the vaginal vault by employing no greater than approximately 100 milligrams of the nonylphenoxypoly (ethyleneoxy) ethanol.

The spermicide composition comprises approximately by weight between 4% and 8% nonylphenoxypoly (ethyleneoxy) ethanol; and between 0.3% and 0.5% pectin; both in a 90% to 94% bacteria-free aqueous solution. Preferably, the composition comprises 8% of the nonylphenoxypoly (ethyleneoxy) ethanol and 0.5% of pectin in 90% distilled water.

One of the major advantages of the invention is the use of a deodorant. Pectin is added to the sponge for this purpose. The sponge also contains at least one preservative and a pH adjusting agent.

From the foregoing compendium, it should be appreciated that it is an object of the present invention to provide a sponge vaginal contraceptive system of the general character described which is not subject to the disadvantages aforementioned.

It is a further aspect of the present invention to provide an improved sponge vaginal contraceptive system of the general character described which is instantaneously available for usage.

It is a further aspect of the present invention to provide a sponge vaginal contraceptive system of the general character described which employs a precisely controlled efficacious dosage of spermicide.

Another feature of the present invention is to provide a sponge vaginal contraceptive system of the general character described which employs but a modicum of spermicide necessary for efficacious usage, thereby reducing adverse side effects.

Other features, aspects and objects of the invention in part will be obvious and in part will be pointed out hereinafter.

With these ends in view, the invention finds embodiment in certain features of construction, combinations of elements, arrangements of parts and series of steps by which the said features, aspects and objects and certain other features, aspects and objects are hereinafter attained, all as fully described with reference to the accompanying drawings and the scope of which is more particularly pointed out and indicated in the appended claims.

BRIEF DESCRIPTION OF THE DRAWINGS

In the accompanying drawings in which is shown one of the various possible embodiments of the invention.

BEST MODE FOR CARRYING OUT THE INVENTION

Figure 1:
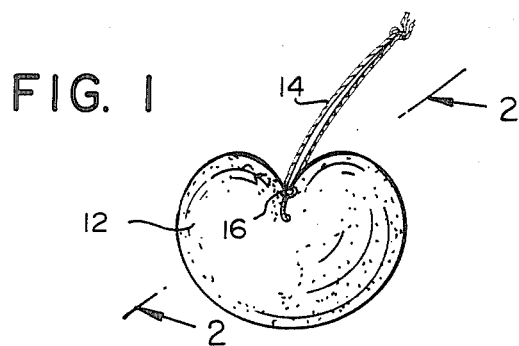
FIG. 1 is a perspective view of a sponge vaginal contraceptive system constructed in accordance with the present invention.
Figure 2:
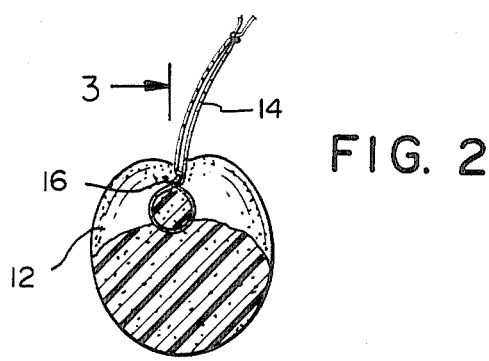
FIG. 2 is a sectional view through the sponge of the contraceptive system, the same being taken substantially along the plane 2—2 of FIG. 1 and illustrating a drawstring looped diametrically through the sponge and compressing an upper area of the sponge.
Figure 3:
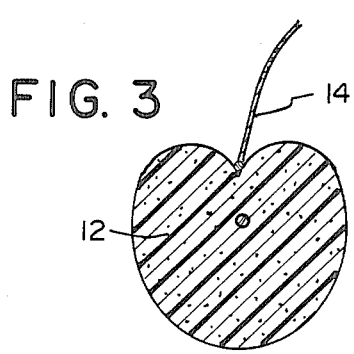
FIG. 3 is a sectional view through the sponge, the same taken substantially along line 3—3 of FIG. 2.

The invention features a sterile, sponge-type contraceptive carrying an active spermicide. A maximum of approximately 100 milligrams of the spermicide is carried in the sponge to keep irritation to the vaginal vault to a minimum, while maintaining effective protection.

The sponge is of a sufficient size and contains swelling agents, so that it will exert radial pressure against the vaginal wall. This prevents slippage, and maintains proper contact between the sponge and the cervix during and throughout its use. The sponge is comfortable to both sex partners, and provides spermicidal activity for 24 hours and through multiple coital episodes.

A significant feature of the vaginal contraceptive system is the inclusion of pectin in the formulation carried by the sponge. Pectin acts as a very effective deodorant, preventing vaginal flora and odors from forming as a function of the vaginal pH. Supplementing the pectin is a pH adjusting agent.

The invention is very simple to use, can be used instantly upon removal from its packet, and generally avoids any serious systemic side effects.

Referring now in detail to the drawings, the reference numeral 10 denotes generally a sponge vaginal contraceptive system constructed in accordance with and embodying the present invention. The system 10 includes a sponge 12 formed of a generally spheroid mass open celled polyurethane having approximately 80 to 100 cells per lineal inch. A string 14 is looped diagonally through the sponge 12 and tied taut in a loop 16 for anchoring purposes. The tied loop 16 compresses and gathers a zone of the sponge, distorting its original spheriod configuration to a reticulated cherry-shaped configuration. The looped string 14 is utilized for withdrawing the sponge 12 from the vaginal vault as will be explained in more detail hereinafter. A knot may be formed at the ends of the looped string 14 to form a second large loop and to assist the user in locating the looped string and extracting the sponge 12.

Figure 4:
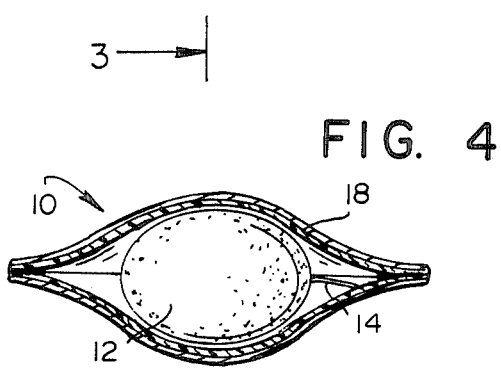
FIG. 4 is a sectional view taken along a vertical plane and through the sponge vaginal contraceptive system of the present invention including a sponge carrying an active spermicide enclosed in a sealed foil packet and ready for instantaneous usage.

As illustrated in FIG. 4, the sponge 12 is packaged in a hermetically sealed sterile foil packet 18 and is impregnated with an active spermicide formulation. The sponge 12 is encased in the packet 18 in a class 100 clean room for sterility. The packet 18 may comprise a foil-thermoplastic film laminate.

The spermicide formulation comprises approximately by weight between 4% and 8% nonylphenoxypoly (ethyleneoxy) ethanol, and between 0.3% and 0.5% pectin, both in a 90% to 94% bacteria-free acqueous solution. Preferably, the composition comprises 8% of the nonylphenoxypoly (ethyleneoxy) ethanol and 0.5% of pectin in 90% distilled water. The pectin constituent controls odor accompanying trichomonas vaginalis as well as non specific vaginitis. It functions as an effective deodorant which prevents vaginal flora and odors from forming as a function of the vaginal pH. Further pH adjusting agents, such as glycine, may also be employed as constituents in the formulation.

A typical active spermicide formulation is shown in the table below:

| | FORMULATION TABLE | | |
|---|---|---|---|
| Ingredient | Function of Ingredients | Composition % | Mg. per Sponge |
| Nonylphenoxypoly (Ethyleneoxy) Ethanol | Spermicide | 8.000 | 100.0000 |
| Pectin | Deodorant | 0.500 | 6.2500 |
| Glycine | pH adjuster | 0.500 | 6.2500 |
| Sodium Carboxymethyl-cellulose | Swelling agent | 0.125 | 1.5625 |
| Methylparaben | Preservative | 0.050 | .6250 |
| Lactic Acid | Bactericide | 0.050 | .6250 |
| Sodium Benzoate | Preservative | 0.100 | 1.2500 |
| Distilled Water | Solvent | 90.675 | 1,133.4375 |
| TOTAL | | 100.000% | 1,250.0000 mg |

The methylparaben is a preservative useful against molds, fungi and yeast. It is also useful against gram positive bacteria.

The sodium benzoate is a preservative that is also useful as a urinary antiseptic against bacteria and mold.

The lactic acid is a bactericide useful in the prevention of leucorrhoea.

The deodorant pectin is also useful as an emulsifier and stabilizing substance, wherein immiscible substances are uniformly dispersed.

Glycine is used in the formulation as pH adjuster to prevent the growth of flora that produces odor. The glycine adjusts the pH to about 4.5 to 5.0. The flora causing the odors usually finds favorable growth in a basic environment.

The sponge 12 is ready for immediate use upon its removal from the packet 18 because the sponge carries the active spermicide formulation. The sponge has a minimum uncompressed peripheral dimension in a transverse diametrical plane of 1.5 to 2.0 inches.

Figure 5:
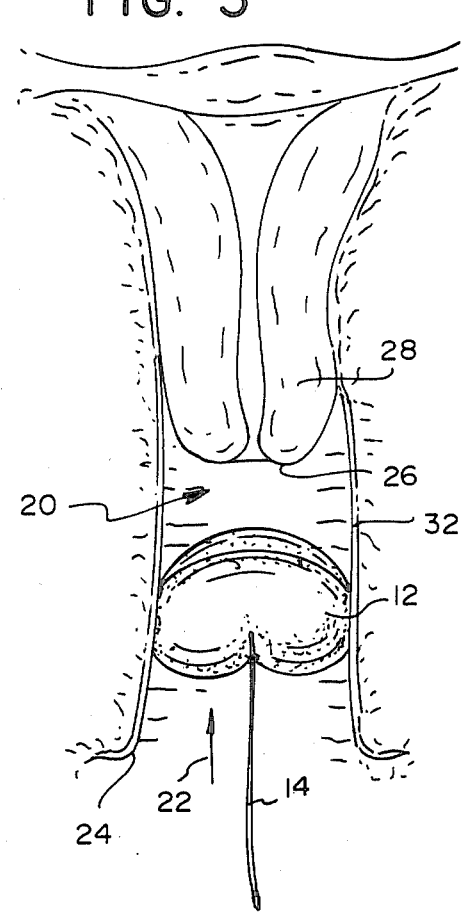
FIG. 5 is a sectional view taken along a vertical plane and through the vaginal vault and showing the sponge being inserted.

The sponge 12 is compressed and urged into the vaginal vault 20 in an upward direction, as indicated by a heavy arrow 22, beyond a vaginal mouth 24 until it abuts a lip 26 of a cervix 28. Such position is depicted in FIG. 5.

Figure 6:
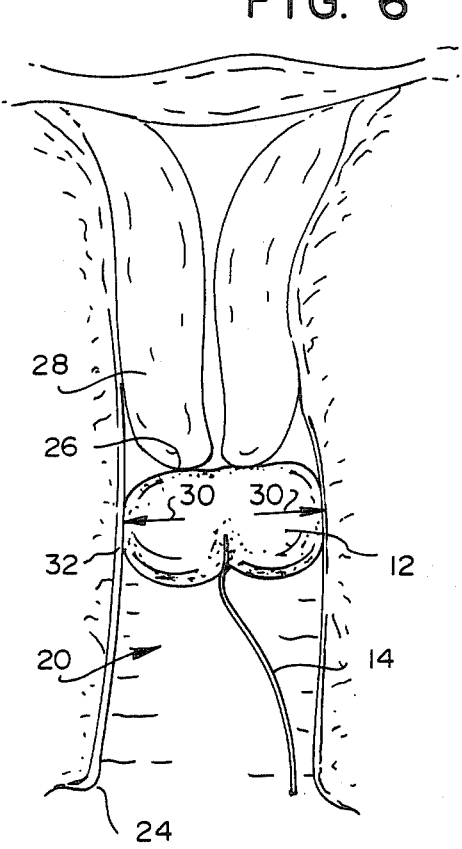
FIG. 6 is a sectional view through the vaginal vault, similar to that of FIG. 4 and showing the sponge in operative position, in contact with the cervix and sealing the vaginal wall.

Referring to FIG. 6, an important function of the contraceptive is schematically shown by a pair of arrows 30. The sponge 12 is made to be sufficiently wide to fill the void across the vaginal wall 32. A minimum uncompressed transverse dimension of approximately 1.8 inches is compatible with practically all women. The transverse plane, wherein the minimum sponge dimension is measured, may typically comprise the horizontal plane of the arrows 30 or any other plane which passes through the sponge when in peripheral contact with the vaginal wall 32.

The sponge 12 is impregnated with a swelling agent, sodium carboxymethylcellulose, which assists in creating radial sponge pressure (schematically illustrated by the arrows 30) against the vaginal wall 32. Such pressure assures that the sponge 12 will fit snugly within the vaginal vault 20 without slippage during and after intercourse. The snug fit provides that the sponge 12 will be maintained in its abutting contact with the lip 26 of the cervix 28. In this position, the sponge 12 will prevent passage of sperm around the vaginal wall 32 and will block entrance of sperm into the womb.

The sponge 12 may be retained in place and provides contraceptive spermicidal activity for 24 hours. It may be removed from the vaginal vault 20 by grasping the looped string 14 and pulling downwardly. The knot which may be located adjacent the end of the drawstring, is useful in locating and pulling the drawstring.

The method of utilizing the sponge contraceptive system of the present invention may be defined by the following steps:

(a) Removing the contraceptive comprising a sponge 12 carrying the active spermicide formulation from the sealed foil packet 18;

(b) Immediately inserting the contraceptive into the vaginal vault 20; and (c) Contacting and blocking the cervix 28 with the sponge 12.

The contraceptive sponge 12 is held in contact with the cervix 28 by the following method step:

(d) Maintaining contact between the sponge 12 and the cervix 28 during and after intercourse by creating radial pressure against the vaginal wall 32.

The contraceptive is removed by the following step:

(e) At least six hours after intercourse but, no greater than 24 hours after insertion, removing the contraceptive sponge 12 from the vaginal vault 20 by grasping the looped string 14 and pulling outwardly.

With respect to the constituents of the spermicidal formulation, the nonylphenoxypoly (ethyleneoxy) ethanol may be obtained from Rohm & Haas Company under the trademark Triton N-101. All of the constituent ingredients of the spermicidal formulation are USP grade and are obtainable from conventional sources. With respect to the sponge 12, suitable polyurethane sponge spheres are obtainable from the Scott Foam Division of the Scott Paper Co.

Thus, it will be seen that there is provided a sponge vaginal contraceptive system of the general character described and method of contraception which achieve the various features, aspects and objects of the invention and which are well suited to meet the conditions of practical employment.

As various possible embodiments might be made of the present invention and some various changes might be made in the exemplary embodiment described herein, it is to be understood that all matter herein described or exemplified is to be interpreted as illustrative rather than in a limiting sense.

Having thus described the invention, there is claimed as new and desired to be secured as Letters Patent:

1. An intravaginal contraceptive porous sponge adapted for immediate use upon removal from a sealed packet and the sponge containing a minimal spermicidally effective amount of nonylphenoxypoly (ethyleneoxy) ethanol as the spermicide in a bacteria-free aqueous solution, pectin and at least one preservative.

2. An intravaginal sponge in accordance with claim 1, wherein the sponge further carries a swelling agent and a pH adjusting agent, the spermicide amounting to about 4% to 8% by weight of the aqueous solution.

3. A sterile intravaginal contraceptive sponge in accordance with claim 2, wherein the spermicide amounts to about 8% and the aqueous solution further contains approximately 0.50% glycine by weight.

4. A sterile intravaginal contraceptive sponge in accordance with claim 2, wherein the sponge further carries lactic acid as a bactericide.

5. An intravaginal spermicidal solution absorbed in a polyurethane sponge sealed in a packet, wherein nonylphenoxypoly (ethyleneoxy) ethanol is the spermicide and comprises approximately 8% by weight of said solution which further contains about 0.50% of pectin by weight of said solution, and said solution being aqueous and bacteria-free.

6. An intravaginal spermicidal solution comprising by weight approximately:

8.00% nonylphenoxypoly (ethyleneoxy) ethanol;
    0.50% pectin;
    0.50% glycine;
    0.125% sodium carboxymethylcellulose;
    0.05% methylparaben;
    0.05% lactic acid; and
    0.10% sodium benzoate, said solution being held in a polyurethane sponge sealed in a packet and ready for immediate use upon removal from said packet.

* * * * *